United States Patent
Wilkinson et al.

(10) Patent No.: US 8,592,213 B2
(45) Date of Patent: Nov. 26, 2013

(54) MARKING FUEL FOR AUTHENTICATION USING QUANTITATIVE AND BINARY MARKERS

(75) Inventors: Timothy G. Wilkinson, York (GB); Erwin Dorland, York (GB)

(73) Assignee: Authentix, Inc., Addison, TX (US)

( * ) Notice: Subject to any disclaimer, the term of this patent is extended or adjusted under 35 U.S.C. 154(b) by 20 days.

(21) Appl. No.: 13/078,101

(22) Filed: Apr. 1, 2011

(65) Prior Publication Data

US 2011/0229983 A1 Sep. 22, 2011

Related U.S. Application Data

(63) Continuation-in-part of application No. PCT/US2008/078775, filed on Oct. 3, 2008.

(51) Int. Cl.
*G01N 33/24* (2006.01)
*G01N 37/00* (2006.01)

(52) U.S. Cl.
USPC ................... 436/27; 436/56; 44/903

(58) Field of Classification Search
USPC ......................... 436/27, 56; 44/903
See application file for complete search history.

(56) References Cited

U.S. PATENT DOCUMENTS

| | | | |
|---|---|---|---|
| 3,862,120 A | 1/1975 | Orelup | |
| 4,141,692 A | 2/1979 | Keller | |
| 5,279,967 A | 1/1994 | Bode | |
| 5,525,516 A | 6/1996 | Krutak et al. | |
| 6,514,917 B1 * | 2/2003 | Smith et al. ................ | 508/184 |
| 8,354,279 B2 * | 1/2013 | Nguyen et al. .............. | 436/27 |
| 2004/0110302 A1 * | 6/2004 | Vamvakaris et al. ........ | 436/56 |
| 2004/0248307 A1 * | 12/2004 | Grof et al. .................... | 436/56 |
| 2007/0212785 A1 * | 9/2007 | Spall et al. .................. | 436/56 |

FOREIGN PATENT DOCUMENTS

| | | |
|---|---|---|
| EP | 1580254 | 9/2005 |
| GB | 361310 | 11/1931 |

OTHER PUBLICATIONS

Arnson, J.F. et al. "Gas chromatographic and associated method for the characterization of oils, fats, waxes and tars. 1982. Methods for the examination of waters and associated materials", Methods for the examination of waters and associated materials, (1982) 59 pages. ISSN: 0141-075X (Abstract Only).*

(Continued)

*Primary Examiner* — Shafiqul Haq
*Assistant Examiner* — Gary E Hollinden
(74) *Attorney, Agent, or Firm* — Conley Rose, P.C.; Rodney B. Carroll

(57) ABSTRACT

A first fuel and a second fuel are marked with a marker that can be detected quantitatively in a predetermined concentration range. The second fuel is marked with a binary marker. Decreased concentration of the quantitative marker, presence of a binary marker, or both may be indicative of a fuel that is altered (e.g., mixed, laundered, diluted, or adulterated). Testing a fuel includes testing the fuel for a presence of a first marker in the fuel in a predetermined concentration range, and testing the fuel for a presence of a second marker. The presence of the first marker in the predetermined concentration range and an absence of the second marker may be indicative that the fuel is unaltered. The presence of the first marker in the fuel in a concentration less than the predetermined concentration range or the presence of the second marker may be indicative that the fuel is altered.

41 Claims, 3 Drawing Sheets

(56) References Cited

OTHER PUBLICATIONS

Ohs, Peter, et al. "Quantitative determination of sudan red dyestuffs in fuel oil and its mixtures with diesel fuels by liquid-chromatography", Fresenius Z Anal Chem (1985) 321:337-341.*

International Search Report and Written Opinion, International Application No. PCT/US2008/078775, dated Jul. 15, 2009, 20 pages.

"Quick tests for Euromarker," Laboratorytalk, Jul. 26, 2004; downloaded from www.laboratorytalk.com on Mar. 30, 2011.

"Euromarker Dyes," Jones Environmental Forensics, Aug. 2002; downloaded from www.jones-forensics.com/technical-information/euromarker-dyes.aspx on Mar. 30, 2011.

Linsinger et al., "Validation of the Draft Community Reference Method for the Determination of Solvent Yellow 124 in Gas Oil (Euromarker)," Institute for Reference Materials and Measurements, 2004.

"Community reference method for the determination of the Euromarker (solvent yellow 124) in gas oils and kerosene," Jul. 13, 2001.

International Preliminary Report on Patentability of International Application No. PCT/US2008/078775, dated Apr. 14, 2011, 9 pages.

* cited by examiner

120
MARKING FUEL FOR AUTHENTICATION USING QUANTITATIVE AND BINARY MARKERS

The present application is a continuation-in-part application of PCT Application No. PCT/US2008/078775, which is hereby incorporated by reference herein.

TECHNICAL FIELD

The present invention relates to marking liquid fuel for authentication purposes.

BACKGROUND

Fuels from different sources may be mixed together to obscure the origin of one or more of the fuels. Fuels from different sources may be, for example, differentially priced fuels, such as taxed fuel and subsidized fuel or tax-free fuel, or different grades or types of fuel, such as kerosene, diesel fuel, low-octane gasoline, high-octane gasoline, and the like. In certain cases, higher priced fuel is mixed with lower priced fuel (e.g., lower grade fuel) or adulterants such as solvents. Fuel may be differentially priced for a variety of reasons. In some countries, liquid fuel, such as diesel fuel, kerosene, and liquefied petroleum gas, is subsidized or sold below market rates to provide more widespread access to resources. Fuel may also be subsidized to protect certain industry sectors, such as public transportation.

In some cases, subsidized fuel is purchased and then re-sold, sometimes illegally, at a higher price. For example, subsidized fuel may be purchased and then mixed with other fuel to disguise the origin of the subsidized fuel. In certain cases, markers placed in subsidized fuel for authentication are at least partially removed to disguise the origin of the fuel.

SUMMARY

One or more fuels are marked to enable detection of a fuel that is altered (e.g., mixed, diluted, laundered, or adulterated). A first fuel and a second fuel are marked with a quantitative marker in a predetermined concentration range. The second fuel is marked with a binary marker. Additional fuels may be marked with additional markers (e.g., a third fuel may be marked with the quantitative marker and a second binary marker). If two or more of the fuels are mixed, concentration of the quantitative marker, presence of a binary marker, or any combination thereof may be indicative that the fuel is altered. A lower concentration of the quantitative marker may be indicative of a mixture of a fuel and an unmarked solvent or different grade fuel or that the fuel has been laundered (the marker deliberately removed from the fuel).

Testing a fuel includes testing the fuel for a presence of a first marker in the fuel in a predetermined concentration range, and testing the fuel for a presence of a second marker. The presence of the first marker in the predetermined concentration range and an absence of the second marker may be indicative that the fuel is unaltered. The presence of the first marker in the fuel in a concentration less than the predetermined concentration range or the presence of the second marker may be indicative that the fuel is altered.

Marking and testing fuels as described herein provide simple, cost-effective, reliable approaches to detecting fuels that are altered, including for example, mixed, diluted, laundered, and adulterated fuels. The methods are advantageously easy to implement and provide improved product integrity.

DETAILED DESCRIPTION

In some cases, a fuel (e.g., a fuel taxed at a higher rate) is combined "as is" with another fuel (e.g., an untaxed fuel or fuel taxed at a lower rate) or solvent to form an altered (e.g., mixed) fuel. As used herein, "altered fuel" is understood to include a fuel that has been mixed, diluted, adulterated, laundered, etc. A fuel may be mixed, for example, with one or more other fuels, solvents, or any combination thereof. If undetected, the altered fuel can be sold, sometimes illegally, at the price of the fuel taxed at the higher rate to yield a profit. The altered fuel can be potentially hazardous for the user.

In certain cases, a fuel is treated or "laundered" in an attempt to remove identifying features such as markers from the fuel (e.g., to disguise the origin of the fuel, the amount of tax paid on the fuel, etc.) before it is mixed with another fuel to form an altered (e.g., mixed) fuel. Marking of fuels that may be potentially mixed allows for identification of altered fuels, even when some of the fuel has been laundered. As described herein, selective marking of fuel that may be potentially mixed to form altered fuel includes marking all of the fuel with a quantitative marker, and additionally marking a portion of the fuel with a second marker. In the case of a quantity of fuel, some of which is to be sold at a higher price (e.g., tax-paid fuel) and some of which is to be sold at a lower price (e.g., tax-paid fuel with a lower tax rate, subsidized fuel, tax-free or untaxed fuel, lower grade fuel), all of the fuel is marked with a first marker, and the portion of the fuel to be sold at the lower price is marked with one or more additional markers (that is, a second marker, a third marker, etc.).

Figure 1:
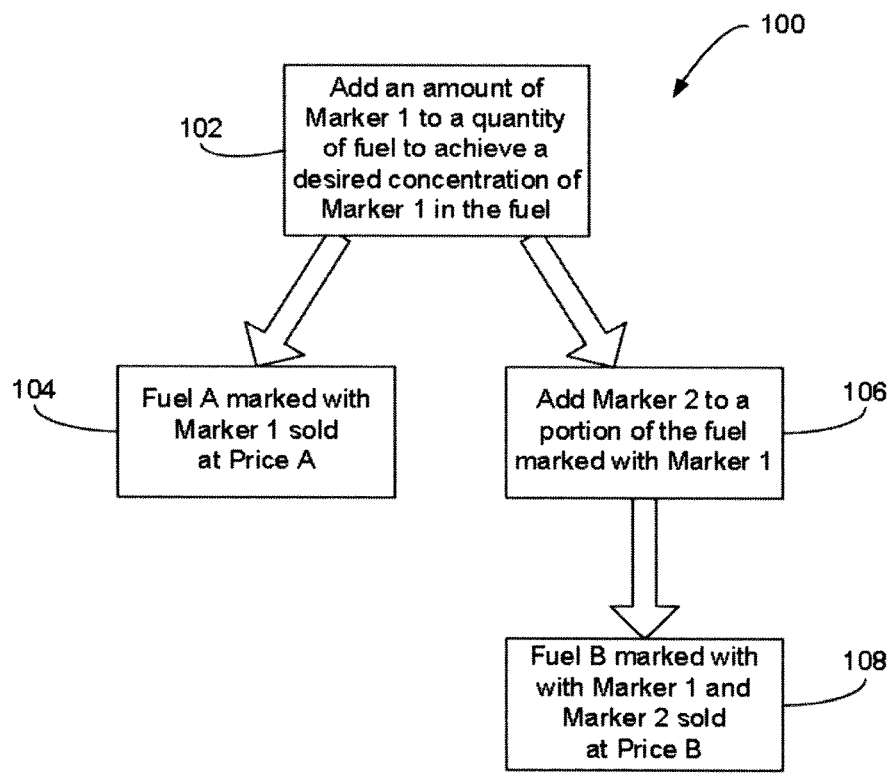
FIG. 1 illustrates a flow diagram for marking of fuel.

FIG. 1 illustrates a method 100 for labeling a quantity of fuel for differential pricing and subsequent detection of a mixture of the differentially priced fuels. In step 102, an amount of a first marker, Marker 1, is added to a quantity of fuel to achieve a desired concentration of Marker 1 in the fuel. The desired concentration may be in a desired concentration range. In step 104, a portion of the fuel including Marker 1 (Fuel A) is priced at Price A. In step 106, a second marker, Marker 2, is added to a portion of the fuel marked with the desired concentration of Marker 1. In step 108, the fuel marked with Marker 1 and Marker 2 (Fuel B) is priced at Price B. When Fuel A is taxed at a high rate and Fuel B is taxed at a lower rate or untaxed, Price A is greater than Price B.

In some embodiments, Marker 1 is a quantitative marker, and Marker 2 is a binary marker. Marker 1 may be a marker at least partially removable by laundering techniques. Marker 2 may be more resistant to one or more laundering techniques, which reduce the concentration of Marker 1 in the fuel. Markers 1 and 2 may be selected such that the presence of Marker 1 does not mask the presence of Marker 2, and the presence of Marker 2 does not mask the presence of Marker 1. In certain embodiments, Fuel A and Fuel B may include one or more additional markers, such as quantitative markers, binary markers, or any combination thereof. For example, Fuel A may include Markers 1 and 1', and Fuel B may include Markers 1, 1', 2, and 2', Markers 1, 2, and 2', Markers 1', 2, and 2', Markers 1, 1', and 2, Markers 1, 1', and 2', etc. Markers 1' and 2 may be quantitative markers, binary markers, or any combination thereof.

In some cases, multiple markers (e.g., multiple binary markers) are used together or separately in one or more fuels to allow detection of a mixture of fuels including fuels taxed at three or more different rates (multiple price differentials). For example, tax-paid Fuel A may include Marker 1, subsidized Fuel B may include Markers 1 and 2, and subsidized Fuel B' (taxed a lower rate than Fuel A and a higher rate than Fuel B) may include Markers 1 and 2'. This allows detection of any combination of Fuels A, B, and B'.

As used herein, a quantitative marker is any marker that can be detected quantitatively. Quantitative markers are used advantageously to detect dilution (i.e., decreased concentration of the marker) caused by mixing, for example, a first fuel with a desired concentration of the quantitative marker and a second fuel that has been treated to remove (or reduce the concentration of) the same quantitative marker. In some cases, as little as 5% or as little as 1% dilution is detectable with the use of quantitative markers. An exemplary quantitative marker includes, for example, the Euromarker Solvent Yellow 124, which is a yellow azo dye used in the European Union as a fuel dye since August 2002.

Testing for the presence of quantitative markers in fuel may be achieved on-site, for rapid determination, or in a laboratory. In some cases, a concentration of a quantitative marker (e.g., a dye) in a fuel is assessed by absorption spectroscopy with ultraviolet, visible, or infrared radiation, in which absorption of radiation by the sample is proportional to the concentration of the marker in the sample. The use and detection of quantitative markers is described in U.S. Pat. No. 5,525,516, which is incorporated herein by reference. In some cases, quantitative markers are extracted from fuel on-site onto an immunoassay column containing antibodies to the marker or solid phase extraction, and then eluted into a vial for analysis using common analytical techniques such as ultraviolet, visible, or infrared radiation.

Quantitative markers exhibit a range of resistance to laundering with, for example, acid, alkali, clay, activated charcoal, diatomaceous earth, or any combination thereof. For example, Solvent Yellow 124 is susceptible to acid, and most visual dyes are removed using activated charcoal.

As used herein, a binary marker is any marker, the presence of which implies the presence of a fuel to which the binary marker was added, and the absence of which implies the absence of a fuel to which the binary marker was added. The binary marker may be a covert or overt tracer. Examples of binary markers includes visual dyes, such as Solvent Red 24.

Some binary markers can be detected by an immunoassay method (including on-site assessment) in which the marker is extracted from the fuel and collected on a chromatography column. Some binary markers (e.g., markers labeled with non-radioactive isotopes) can be effectively detected at very low levels in a laboratory setting by gas chromatography/mass spectrometry, in which a sample is vaporized and components are identified by molecular weight. Some binary markers with characteristic vibrational and/or rotational modes are detectable by a reader using, for example, infrared spectroscopy to read a sample of the fuel and provide an indication that the marker is present when a portion of the spectrum (e.g., infrared or XRF) corresponds to the signature of the marker (e.g., infrared or XRF, respectively).

Binary markers exhibit a range of resistance to laundering with, for example, acid, alkali, clay, diatomaceous earth, or any combination thereof. Some binary markers are highly resistant to laundering with acid, alkali, activated charcoal, clay, and diatomaceous earth. Marking a differentially priced fuel with two or more markers that exhibit different resistance to various laundering techniques allows detection of mixed fuels, at least one of which has been treated to remove one or more of the markers. When analytical techniques are used to detect the quantitative marker, the binary marker, or both, traces of markers may be detected in fuels that were treated to remove the markers. More advanced laboratory techniques may be used to confirm very low levels of markers, ranging from low ppm to ppt levels.

Table I shows examples of useful combinations of quantitative and binary markers, as characterized by laundering properties.

TABLE I

Examples of dual marker combinations for detection of altered fuel

| Marker Combination | Quantitative Marker | Binary Marker |
|---|---|---|
| 1 | Removed by acid and clay; Resistant to alkali | Removed by acid and diatomaceous earth; Resistant to alkali |
| 2 | Removed by alkali and clay; Resistant to acid | Removed by alkali; Resistant to acid and clay |

As Table I shows, for Marker Combination 1, both quantitative and binary markers can be removed by, or substantially removed by, acid and clay, and are resistant to alkali. For Marker Combination 2, the quantitative marker can be removed by, or substantially removed by, alkali and clay, and the binary marker is removed by, or substantially removed by, alkali. The quantitative marker is resistant to acid, and the binary marker is resistant to acid and clay. That is, for marker pairs used to label differentially priced fuel, it is desirable for both the quantitative marker and the binary marker to be susceptible to laundering with at least one of the same agents. Additionally, it is also advantageous when the quantitative marker is more susceptible to laundering by a particular agent than the paired binary marker, such that a lower concentration of the quantitative marker, the presence of the binary marker, or a combination thereof is detectable. Marker combinations may be advantageously chosen such that the markers do not interfere with each other (i.e., the markers do not mask each other).

Marked combinations may be chosen such that:

i) If an unaltered fuel (e.g., a fuel which has not undergone a laundering process) with Marker 1 and Marker 2 is mixed with an unaltered fuel with only Marker 1, the presence of Marker 2 is detectable in the mixed fuel. The mixed fuel, by nature of mixing two different fuels, may be referred to as an altered fuel.

ii) If a fuel with Marker 1 and Marker 2 is laundered to remove at least some of Marker 1 and mixed with an unaltered fuel with only Marker 1, a lower concentration of Marker 1 is detectable in the mixed (altered) fuel.

iii) If a fuel with Marker 1 and Marker 2 is laundered to remove at least some of Marker 1 and at least some of Marker 2 and mixed with an unaltered fuel with only Marker 1, a lower concentration of Marker 1, the presence of Marker 2, or a combination thereof is detectable in the mixed (altered) fuel.

iv) If a fuel with Marker 1 and Marker 2 is laundered to remove substantially all of Marker 1 and substantially all of Marker 2 and mixed with an unaltered fuel with only Marker 1, a lower concentration of Marker 1 is detectable in the mixed (altered) fuel.

v) If a fuel with only Marker 1 is laundered to remove at least some of Marker 1 and mixed with an unaltered fuel with Marker 1 and Marker 2, a lower concentration of Marker 1, the presence of Marker 2, or a combination thereof is detectable in the mixed (altered) fuel.

vi) If a solvent is mixed with any fuel with a quantitative marker, a lower concentration of the marker is detectable in the mixed (altered or diluted) fuel.

Figure 2:
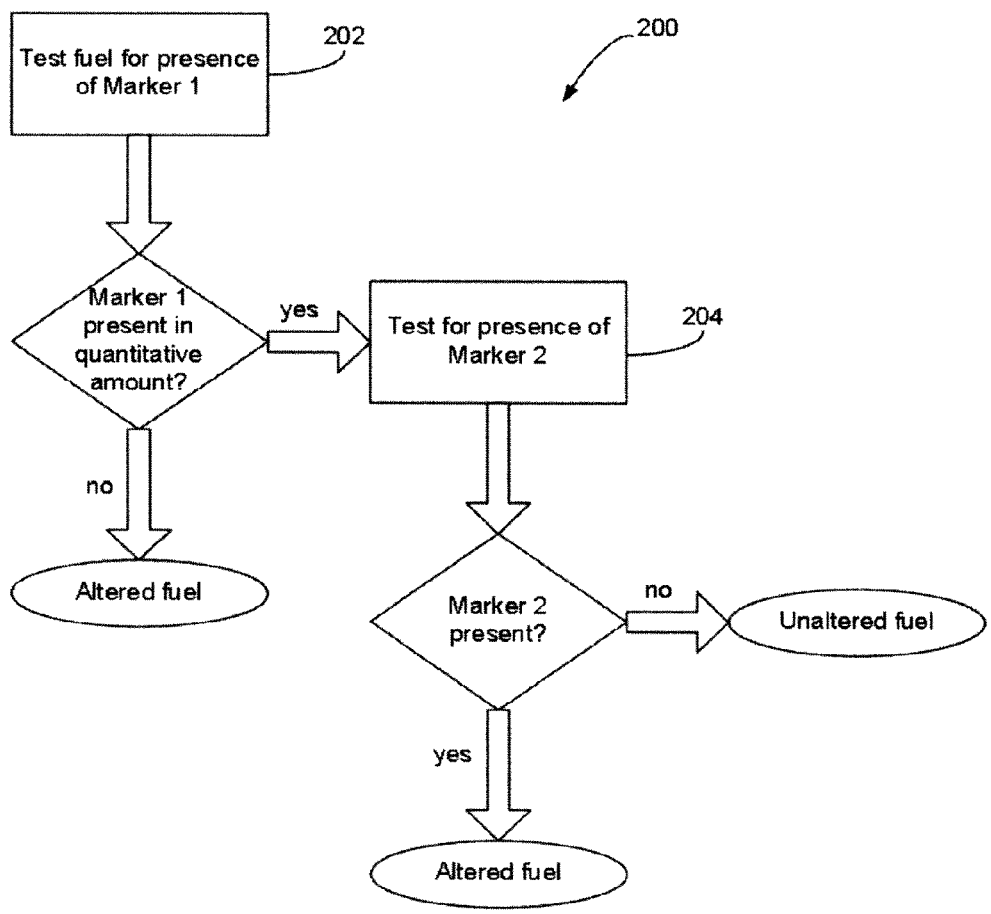
FIG. 2 illustrates a flow diagram for testing for mixed fuel.
Figure 3:
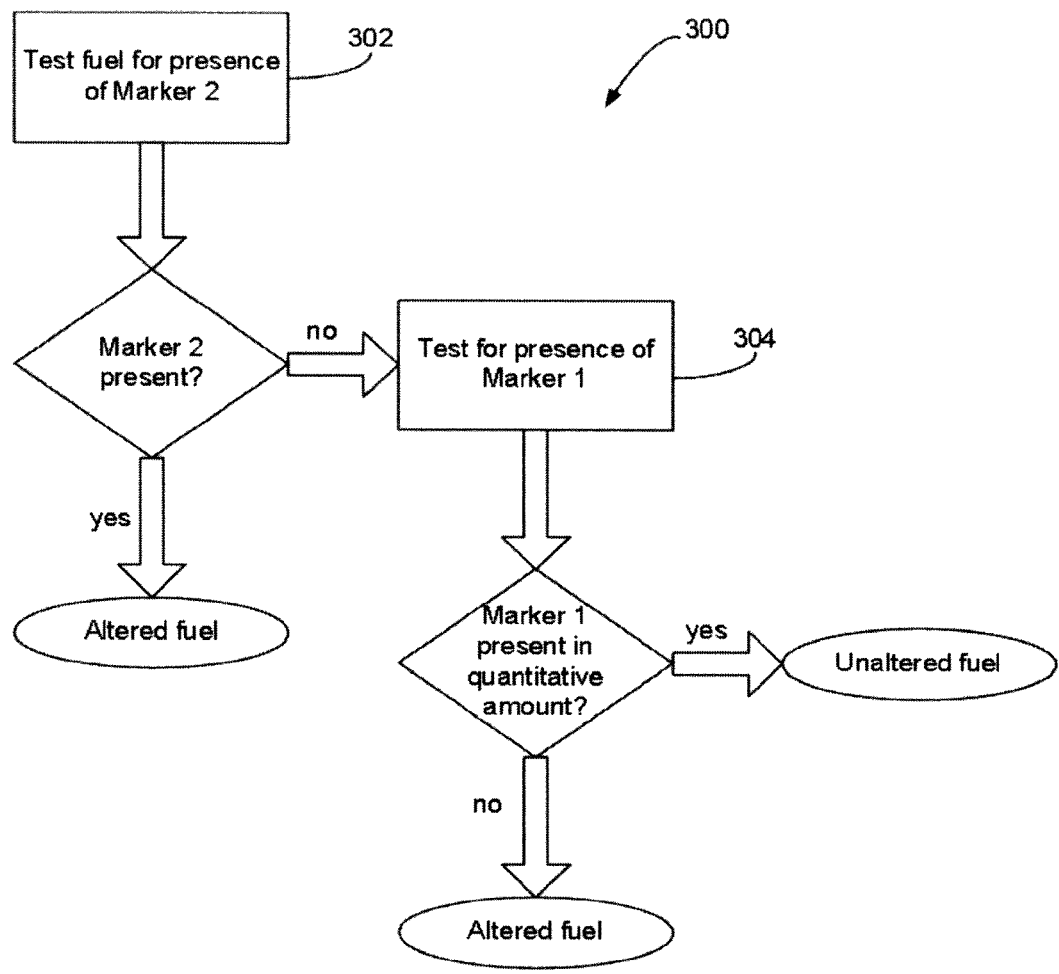
FIG. 3 illustrates a flow diagram for testing for mixed fuel.

FIGS. 2 and 3 illustrate methods 200 and 300, respectively, for determining if a fuel is an altered fuel including a mixture of i) a first fuel marked with Marker 1 in a predetermined concentration range (a quantitative marker) (e.g., Fuel A) and a second fuel marked with Marker 1 in the same predetermined concentration range and Marker 2 (a binary marker) (e.g., Fuel B); ii) a first fuel marked with Marker 1 (e.g., Fuel A) in a predetermined concentration range and a solvent, etc.

In FIG. 2, a fuel (e.g., a tax-paid fuel or high tax rate fuel) is tested 202 for the presence of Marker 1. If Marker 1 is not detected in a quantitative amount (i.e., if Marker 1 is determined to be at a concentration lower than the predetermined concentration range of, for example, Fuel A), then the fuel is determined to be an altered fuel, possibly including a portion of fuel (e.g., Fuel B) from which Marker 1 has been at least partially removed or a portion of fuel or solvent to which Marker 1 was never added. If Marker 1 is present in a quantitative amount (i.e., in a predetermined concentration range), then the fuel is determined to be either an unaltered fuel (e.g., Fuel A) or an altered fuel (e.g., mixture of two fuels (e.g., Fuel A and Fuel B) with substantially the same concentration of Marker 1). The fuel is then tested 204 for the presence of Marker 2, which may be present in altered fuel that includes a taxed fuel (e.g., Fuel A) and a subsidized fuel (e.g., Fuel B). If Marker 2 is not detected, the fuel is determined to be an unaltered or unmixed (e.g., unadulterated) fuel (e.g., Fuel A). If Marker 2 is detected, then the fuel is determined to have been altered or mixed with another (e.g., lower priced, lower grade, etc.) fuel (e.g., Fuel B) with substantially the same concentration of Marker 1 (e.g., the fuel is a mixture of Fuel A and Fuel B). Detection techniques, such as on-site immunoassay methods, may allow for detection of Marker 2 even if the marker has been at least partially removed in a laundering operation.

In FIG. 3, a fuel is tested 302 for the presence of Marker 2. If Marker 2 is detected, then the fuel is determined to be a fuel resulting from a mixture of a lower priced fuel marked with Marker 2 (e.g., Fuel B) and a higher priced fuel (e.g., Fuel A). If Marker 2 is not detected, then the fuel is determined to be either an unaltered fuel (e.g., Fuel A), or an altered fuel (e.g., a mixture of Fuel A and Fuel B) that may include a component (e.g., Fuel B) from which Marker 2 has been at least partially removed. The fuel is then tested 304 for the presence of Marker 1. If Marker 1 is detected in the predetermined concentration range, then the fuel is determined to be unaltered (e.g., unmixed Fuel A). If Marker 1 is detected in a concentration below the predetermined concentration range, then the fuel is determined to be altered (e.g., a mixture of Fuel A and Fuel B, a mixture of Fuel A and a solvent, laundered Fuel A, etc.).

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
adding a first marker to a fuel;
obtaining a sample of fuel having an unknown number of markers;
testing the fuel for a presence of the first marker in the fuel in a predetermined concentration range; and
testing the fuel for a presence of a second marker in the fuel wherein:
the presence of the first marker in the fuel in the predetermined concentration range and an absence of the second marker in the fuel is indicative that the fuel is unaltered,
the presence of the first marker in the fuel in a concentration less than the predetermined concentration range is indicative that the fuel is altered, and
the presence of the second marker in the fuel is indicative of an altered fuel,
wherein the testing the fuel for the presence of the first marker and testing the fuel for the presence of the second marker are performed a substantial period of time subsequent to the adding of the first marker to the fuel; the first marker is a quantitative marker, the second marker is a binary marker, the first marker and the second marker are each configured so that each can be at least partially removed from the fuel by the same laundering agent and testing of the fuel occurs on-site.

2. The method as recited in claim 1, wherein testing the fuel for the presence of the first marker comprises ultraviolet, visible, infrared, or x-ray fluorescence spectroscopy.

3. The method as recited in claim 1, wherein testing the fuel for the presence of the second marker comprises performing gas chromatography/mass spectrometry, liquid chromatography/mass spectrometry, or any combination thereof.

4. The method as recited in claim 1, wherein the first marker is configured so that a presence of the first marker in the fuel does not mask a presence of the second marker in the fuel, and the second marker is configured so that a presence of the second marker in the fuel does not mask a presence of the first marker in the fuel.

5. The method as recited in claim 1, wherein at least a portion of the fuel has been treated to remove at least one of the markers during a time subsequent to when at least the first marker was added to the fuel and prior to when the fuel is tested for the presence of the first marker and the second marker.

6. The method as recited in claim 5, wherein the portion of the fuel has been treated to remove the first marker, and treatment to remove the first marker leaves a detectable amount of the second marker in the portion of the fuel.

7. The method as recited in claim 5, wherein the portion of the fuel has been treated to remove the second marker, and treatment to remove the second marker substantially removes the first marker from the portion of the fuel.

8. The method as recited in claim 7, wherein the portion of the fuel has been treated with acid, alkali, active charcoal, clay, diatomaceous earth, or any combination thereof.

9. The method as recited in claim 1, further comprising testing the fuel for a presence of a third marker in the fuel, wherein:
the presence of the first marker in the fuel in the predetermined concentration range, the absence of the second marker in the fuel, and an absence of the third marker in the fuel is indicative that the fuel is unaltered,
the presence of the first marker in the fuel in a concentration less than the predetermined concentration range is indicative that the fuel is altered,
the presence of the second marker in the fuel is indicative that the fuel is altered, and
the presence of the third marker in the fuel is indicative that the fuel is altered.

10. The method as recited in claim 1, wherein an altered fuel is a mixed fuel, a diluted fuel, or a laundered fuel.

11. A method of marking a first fuel and a second fuel to allow detection of a mixture of the first fuel and the second fuel, the method comprising marking the first fuel and the second fuel with a first marker in a predetermined concentration range, and marking the second fuel with a second marker, wherein the first marker is a quantitative marker and the second marker is a binary marker; wherein testing of the fuel occurs on-site and the first marker and the second marker are each configured so that each can be at least partially removed from the fuel by the same treatment, laundering agent, or any combination thereof.

12. The method as recited in claim 11, wherein the first marker is detectable by ultraviolet, visible, infrared, or XRF spectroscopy, or any combination thereof.

13. The method as recited in claim 11, wherein the second marker is detectable by ultraviolet, visible, infrared, or XRF spectroscopy, or any combination thereof.

14. The method as recited in claim 13, wherein the second marker is detectable by gas chromatography/mass spectrometry, liquid chromatography/mass spectrometry, or any combination thereof.

15. The method as recited in claim 11, wherein the first marker is configured so that a presence of the first marker in the fuel does not mask a presence of the second marker in the fuel, and the second marker is configured so that a presence of the second marker in the fuel does not mask a presence of the first marker in the fuel.

16. The method as recited in claim 11, wherein the first marker and the second marker are resistant to removal from the fuel by substantially the same treatment, laundering agent, or any combination thereof.

17. The method as recited in claim 11, wherein treatment of the second fuel to remove the first marker from the second fuel leaves a detectable amount of the second marker in the second fuel.

18. The method as recited in claim 11, wherein treatment of the second fuel to remove the second marker from the second fuel substantially removes the first marker from the second fuel.

19. The method as recited in claim 16, wherein treatment of the second fuel comprises treatment with acid, alkali, active charcoal, clay, diatomaceous earth, or any combination thereof.

20. The method as recited in claim 11, further comprising marking a third fuel with the first marker in the predetermined concentration range and a third marker, wherein the third marker is a binary marker.

21. A method for determining whether a hydrocarbon fuel has been altered subsequent to a time when a first marker has been added to the fuel, the method comprising:
   obtaining a sample of fuel having an unknown number markers;
   testing the fuel for a presence of the first marker in the fuel;
   if the first marker is present in the fuel, then testing the fuel for a presence of a second marker in the fuel;
   determining that the fuel is an altered fuel if the second marker is present in the fuel; and
   determining that the fuel is an unaltered fuel if the second marker is not present in the fuel wherein the first marker and the second marker are each configured so that each can be at least partially removed from the fuel by the same laundering agent the first marker is a quantitative marker and the second marker is a binary marker and testing of the fuel occurs on-site.

22. The method as recited in claim 21, wherein the first marker is configured so that a presence of the first marker in the fuel does not mask a presence of the second marker in the fuel, and the second marker is configured so that a presence of the second marker in the fuel does not mask a presence of the first marker in the fuel.

23. The method as recited in claim 21, wherein the fuel has previously had at least a portion of at least one of the markers removed by a treatment process.

24. The method as recited in claim 21, wherein previous to the testing of the fuel, a portion of the fuel was treated to remove the first marker, which leaves a detectable amount of the second marker in the portion of the fuel.

25. The method as recited in claim 21, wherein previous to the testing of the fuel, a portion of the fuel was treated to remove the second marker, which substantially removes the first marker from the portion of the fuel.

26. The method as recited in claim 21, wherein an altered fuel is a mixed fuel.

27. The method as recited in claim 21, wherein an altered fuel is a diluted fuel.

28. The method as recited in claim 21, wherein an altered fuel is a laundered fuel.

29. The method as recited in claim 21, further comprising determining that the fuel is an altered fuel if the first marker is not present in the fuel.

30. The method as recited in claim 1, wherein the testing the fuel for the presence of the first marker and the testing the fuel for the presence of the second marker are performed subsequent to the fuel being commercially sold with the first marker present in the fuel.

31. The method as recited in claim 1, wherein presence of the second marker in the fuel is unknown by a person performing the testing of the fuel for the first marker and the second marker.

32. The method as recited in claim 1, wherein testing for the presence of the second marker in the fuel is testing for the presence of any detectable concentration of the second marker in the fuel.

33. The method as recited in claim 21, wherein the testing the fuel for the presence of the first marker is performed a substantial period of time subsequent to the time when the first marker had been added to the fuel.

34. A method for determining whether a fuel has been altered subsequent to a time when a first marker has been added to the fuel, the method comprising:
   obtaining a sample of fuel having an unknown number markers;
   testing the fuel for a presence of the first marker in the fuel in a predetermined concentration range; and
   testing the fuel for a presence of a second marker in the fuel, wherein:
      the presence of the first marker in the fuel in the predetermined concentration range and an absence of the second marker in the fuel is indicative that the fuel is unaltered,
      the presence of the first marker in the fuel in a concentration less than the predetermined concentration range is indicative that the fuel is altered, and
      the presence of the second marker in the fuel is indicative of an altered fuel wherein the first marker and the second marker are each configured so that each can be at least partially removed from the fuel by the same laundering agent; the first marker is a quantitative marker and the second marker is a binary marker and testing of the fuel occurs on-site.

35. The method as recited in claim 34, wherein at least a portion of the fuel has been treated to remove at least one of the markers during a time subsequent to when at least the first marker was added to the fuel and prior to when the fuel is tested for the presence of the first marker and the second marker.

36. The method as recited in claim 34, wherein an altered fuel is a fuel that has been mixed with another different fuel.

37. The method as recited in claim 34, wherein an altered fuel is a diluted fuel.

38. The method as recited in claim 34, wherein an altered fuel is a laundered fuel.

39. The method as recited in claim 34, wherein an unaltered fuel has not been mixed with another different fuel, has not been diluted, or has not been laundered.

40. A method comprising:
  obtaining a sample of fuel having an unknown number markers;
  testing the fuel for a presence of a first marker in the fuel in a predetermined concentration range; and
  testing the fuel for a presence of a second marker in the fuel, wherein:
    the presence of the first marker in the fuel in the predetermined concentration range and an absence of the second marker in the fuel is indicative that the fuel is unaltered,
    the presence of the first marker in the fuel in a concentration less than the predetermined concentration range is indicative that the fuel is altered, and
    the presence of the second marker in the fuel is indicative of an altered fuel, wherein testing the fuel for the presence of the first marker comprises infrared or x-ray fluorescence spectroscopy wherein the first marker and the second marker are each configured so that each can be at least partially removed from the fuel by the same laundering agent; the first marker is a quantitative marker and the second marker is a binary marker; and testing of the fuel occurs on-site.

41. A method comprising:
  obtaining a sample of fuel having an unknown number markers;
  testing the fuel for a presence of a first marker in the fuel in a predetermined concentration range;
  testing the fuel for a presence of a second marker in the fuel, wherein:
    the presence of the first marker in the fuel in the predetermined concentration range and an absence of the second marker in the fuel is indicative that the fuel is unaltered,
    the presence of the first marker in the fuel in a concentration less than the predetermined concentration range is indicative that the fuel is altered, and
    the presence of the second marker in the fuel is indicative of an altered fuel; and
  testing the fuel for a presence of a third marker in the fuel, wherein:
    the presence of the first marker in the fuel in the predetermined concentration range, the absence of the second marker in the fuel, and an absence of the third marker in the fuel is indicative that the fuel is unaltered,
    the presence of the first marker in the fuel in a concentration less than the predetermined concentration range is indicative that the fuel is altered,
    the presence of the second marker in the fuel is indicative that the fuel is altered, and
    the presence of the third marker in the fuel is indicative that the fuel is altered wherein the first marker and the second marker are each configured so that each can be at least partially removed from the fuel by the same laundering agent; at least one of the markers is a quantitative marker and at least one of the markers is a binary maker and testing of the fuel occurs on-site.

* * * * *